United States Patent
Karlsson

(10) Patent No.: US 10,458,984 B2
(45) Date of Patent: Oct. 29, 2019

(54) METHOD AND SYSTEM FOR INTERACTION ANALYSIS

(71) Applicant: GE Healthcare Bio-Sciences AB, Uppsala (SE)

(72) Inventor: Robert Karlsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 396 days.

(21) Appl. No.: 15/113,352

(22) PCT Filed: Jan. 29, 2015

(86) PCT No.: PCT/EP2015/051834
§ 371 (c)(1),
(2) Date: Jul. 21, 2016

(87) PCT Pub. No.: WO2015/114056
PCT Pub. Date: Aug. 6, 2015

(65) Prior Publication Data
US 2017/0038379 A1    Feb. 9, 2017

(30) Foreign Application Priority Data

Jan. 29, 2014  (SE) ...................................... 1450083

(51) Int. Cl.
*G06F 19/22* (2011.01)
*G01N 33/557* (2006.01)
(Continued)

(52) U.S. Cl.
CPC ..... *G01N 33/557* (2013.01); *G01N 33/54373* (2013.01); *G16B 30/00* (2019.02)

(58) Field of Classification Search
CPC .... G01N 33/6845; G01N 33/68; G01N 35/08; G01N 27/3274; G01N 21/553;
(Continued)

(56) References Cited

U.S. PATENT DOCUMENTS 5,242,828 A    9/1993  Bergström et al.
5,313,264 A    5/1994  Ivarsson et al.
(Continued)

FOREIGN PATENT DOCUMENTS

CN    102667448 A    9/2012
EP    1643238 A1 *  4/2006
(Continued)

OTHER PUBLICATIONS

Gomes et al., "Direct kinetic assay of interactions between small peptides and immobilized antibodies using a surface plasmon resonance biosensor", Journal of Immunological Methods, Elsevier Science Publishers B.V., Amsterdam, NL, Jan. 1, 2002, vol. 259, No. 1-2, pp. 217-230.
(Continued)

*Primary Examiner* — Mary K Zeman
(74) *Attorney, Agent, or Firm* — Hanley, Flight & Zimmerman, LLC

(57) ABSTRACT

A method for evaluation of an interaction between an analyte in a fluid sample and a ligand immobilized on a sensor surface of a biosensor, which comprises the steps of: providing a reference binding curve, representing a reference interaction for a predetermined acquisition cycle, acquiring, using the biosensor, a sample binding curve for the analyte ligand interaction for the predetermined acquisition cycle,
registering the deviation of the sample binding curve from the reference binding curve, and
classifying the analyte ligand interaction as equivalent to the reference interaction when the registered deviation is less than a predetermined deviation criteria. There is further provided a biosensor system and a computer program.

19 Claims, 22 Drawing Sheets

(51) Int. Cl.
*G01N 33/543* (2006.01)
*G16B 30/00* (2019.01)

(58) Field of Classification Search
CPC ......... G01N 35/085; G01N 2035/0097; G01N 21/55; G01N 33/53; G01N 2500/20; G01N 33/6803; G01N 30/86; G01N 33/487; C12Q 2537/165; C12Q 2527/101; C12Q 1/6827; C12Q 1/005; C12Q 1/006; C12Q 2527/107; C12Q 2545/101; C12Q 1/6816; G06F 19/22; G06F 19/24; G06F 19/26; G16B 30/00; G16B 40/00; G16B 45/00

See application file for complete search history.

(56) References Cited

U.S. PATENT DOCUMENTS

| | | | |
|---|---|---|---|
| 5,436,161 | A | 7/1995 | Bergström et al. |
| 5,492,840 | A | 2/1996 | Malmqvist et al. |
| 9,316,636 | B2 * | 4/2016 | Karlsson ............... G01N 33/543 |
| 2007/0048807 | A1 | 3/2007 | Song |
| 2008/0145838 | A1 | 6/2008 | Yasuo et al. |
| 2012/0100567 | A1 * | 4/2012 | Kaneda ................. C12Q 1/005 435/25 |
| 2018/0224439 | A1 * | 8/2018 | Karlsson ................ G06F 19/26 |

FOREIGN PATENT DOCUMENTS

| | | | |
|---|---|---|---|
| EP | 2034313 | * | 3/2009 |
| EP | 2034313 A1 | | 3/2009 |
| JP | H04-130270 A | | 5/1992 |
| JP | 2004-257741 A | | 9/2004 |
| JP | 2006-105610 A | | 4/2006 |
| JP | 2008-544248 A | | 12/2008 |
| JP | 2011-217747 A | | 11/2011 |
| WO | 97/43644 A1 | | 11/1997 |
| WO | 2006/047760 A1 | | 5/2006 |
| WO | 2006/135309 A2 | | 12/2006 |
| WO | 2011/065913 A1 | | 6/2011 |
| WO | 2011/093782 A1 | | 8/2011 |
| WO | WO2012/118433 | * | 1/2012 |
| WO | 2012/054886 A1 | | 4/2012 |
| WO | 2012/061778 A2 | | 5/2012 |
| WO | 2012/118433 A1 | | 9/2012 |
| WO | 2013/066986 A1 | | 5/2013 |

OTHER PUBLICATIONS

Hahnefeld et al., "Determination of Kinetic Data Using Surface Plasmon Resonance Biosensors", Methods in Molecular Medicine, Humana Press, Totwa, NJ, US, Dec. 1, 2003, vol. 94, pp. 299-320.
Cheskis et al., "Modulation of Nuclear Receptor Interactions by Ligands: Kinetic Analysis Using Surface Plasmon Resonance", Biochemistry, American Chemical Society, US, Jan. 1, 1996, vol. 35, No. 10, pp. 3309-3318.
International Search Report and Written Opinion regarding International Application No. PCT/EP2015/051834, dated May 8, 2015, 14 pages.
International-Type Search Report regarding SE Application No. 1450083-9, dated Jul. 18, 2014, 5 pages.
Malmqvist, M., "BIOCORE: An affinity biosensor system for characterization of biomolecular interactions," Biosensors: Into the 21st Century, vol. 27, pp. 335-340 (1999).
Yuanyuan, C., et al., "New Biosensor Technology Based on Surface Plasmon Resonance and Its Application in life sciences," Journal of Biophysics, vol. 22, Issue 2, pp. 82-88 (Apr. 30, 2006).
First Office Action and Search issued in connection with corrsponding CN Application No. 201580006412.9 dated Sep. 28, 2017.
"Biacore T200," GE Healthcare Life Sciences, Instrument Handbook, Retrieved from Internet URL: https://www.gelifesciences.co.jp/tech_support/manual/pdf/71341633_biacore_t200_app.pdf, Retrieved on Dec. 24, 2018, pp. 1-189 (English Translation not available).
Notification of Reasons for Refusal issued in connection with corresponding JP Application No. 2016-548310 dated Oct. 23, 2018.

* cited by examiner

MabX-ECR reagent 3154    pH stressed spiked

MabX-ECR reagent 3154    Oxidized spiked

MabX ECR reagent 2994 spiked data pH stressed Mab X

MabX ECR reagent 2994 spiked data

Oxidized Mab X

METHOD AND SYSTEM FOR INTERACTION ANALYSIS

CROSS-REFERENCE TO RELATED APPLICATIONS

This application is a filing under 35 U.S.C. 371 of international application number PCT/EP2015/051834, filed Jan. 29, 2015, which claims priority to SE application number 1450083-9, filed Jan. 29, 2014, the entire disclosures of each of which are hereby incorporated by reference.

FIELD OF THE INVENTION

The present invention relates to a method of evaluation of molecular binding interactions at a sensing surface, and more particularly to a method for evaluation of an interaction between an analyte in a fluid sample and a ligand immobilized on a sensor surface of a biosensor that is independent of interaction models.

BACKGROUND OF THE INVENTION

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by GE Healthcare, which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a binding curve or "sensorgram".

With the BIACORE® system (and analogous sensor systems) it is thus possible to determine in real time without the use of labeling, and often without purification of the substances involved, not only the presence and concentration of a particular molecule (analyte) in a sample, but also additional interaction parameters, including kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants.

In order to derive the above interaction parameters from registered binding curves there has been developed a range of different assays and models involving more or less complex calculations which have proven to give very reliable results for many types of interactions. However, many of these calculations are based on a specific interaction model and thus are limited to interactions of a specific type that fall under this model and there are a range of interactions that are not easily categorized according to a specific model. Therefore, it is not always possible to provide reliable interaction parameters for evaluation of some analyte ligand interactions. FIG. 3 disclose two schematic examples of binding curves where the model based evaluation (dashed line) was not able to provide reliable results.

One alternative method to evaluate this type of interactions is to rely on report points at predetermined points in the binding curve. But in analysis based on report points, only information about the interaction at the specific report points is used to characterize the interaction, whereas a majority of the information in the binding curves is discarded.

SUMMARY OF THE INVENTION

The object of the invention is to provide a new method and biosensor system for evaluation of an interaction between an analyte in a fluid sample and a ligand immobilized on a sensor surface of a biosensor, which method and biosensor system overcomes one or more drawbacks of the prior art. This is achieved by the method and biosensor system as defined in the independent claims.

One advantage with the method and biosensor system of the present invention is that it allows evaluation of analyte ligand interactions that is independent of theoretical interaction models, while still taking all registered data points into account. Another advantage is that the evaluation is less complex compared to prior art evaluation methods, and therefore requires less computational power.

A more complete understanding of the present invention, as well as further features and advantages thereof, will be obtained by reference to the following detailed description and drawings.

DETAILED DESCRIPTION OF THE INVENTION

Figure 1:
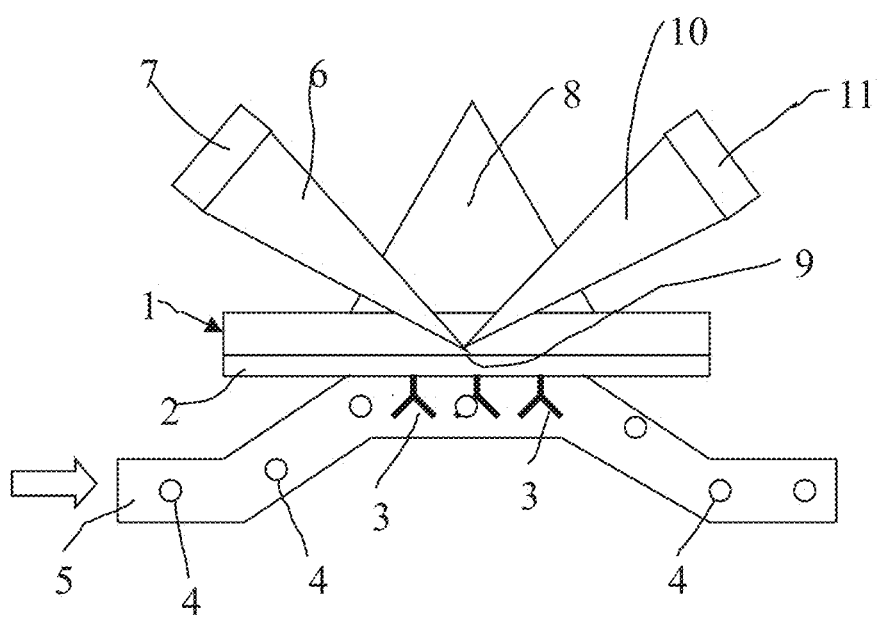
FIG. 1 is a schematic side view of a biosensor system based on SPR.

As mentioned above, the present invention relates to a method and a biosensor system for evaluation of an interaction between an analyte in a fluid sample and a ligand immobilized on a sensor surface of a biosensor.

Typically, the experimental binding data is obtained by sensor-based technology, which studies the molecular interactions and presents the results in real time as the interactions progress. Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers (e.g. Bio-Layer Interferometry as implemented by ForteBio®), waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by GE Healthcare, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip, which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or curve (binding isotherm), is usually called binding curve or sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated in the binding curve by an increase in RU as the sample is initially brought into contact with the sensor surface. Conversely, "dissociation" normally occurs when the sample flow is replaced by, for example, a buffer flow. This step is indicated in the binding curve by a drop in RU over time as analyte dissociates from the surface-bound ligand.

Figure 2:
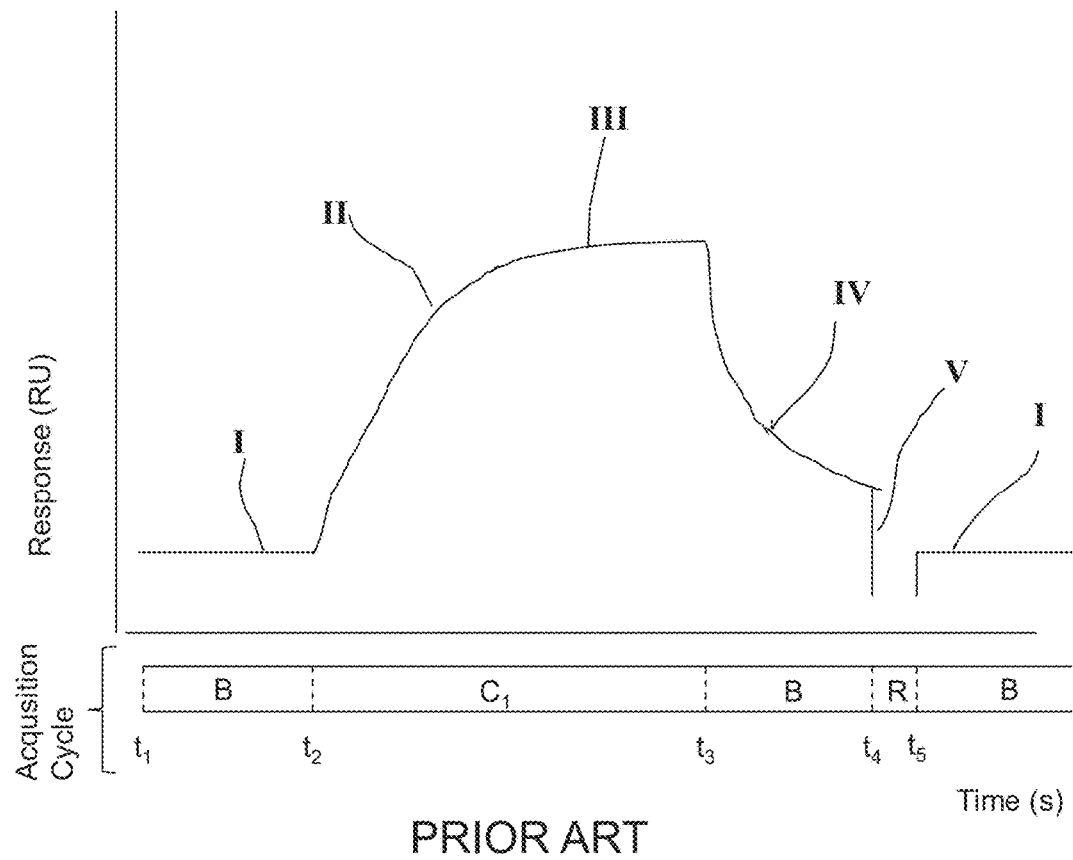
FIG. 2 is a representative sensorgram where the binding curve has visible association and dissociation phases.
Figure 3:
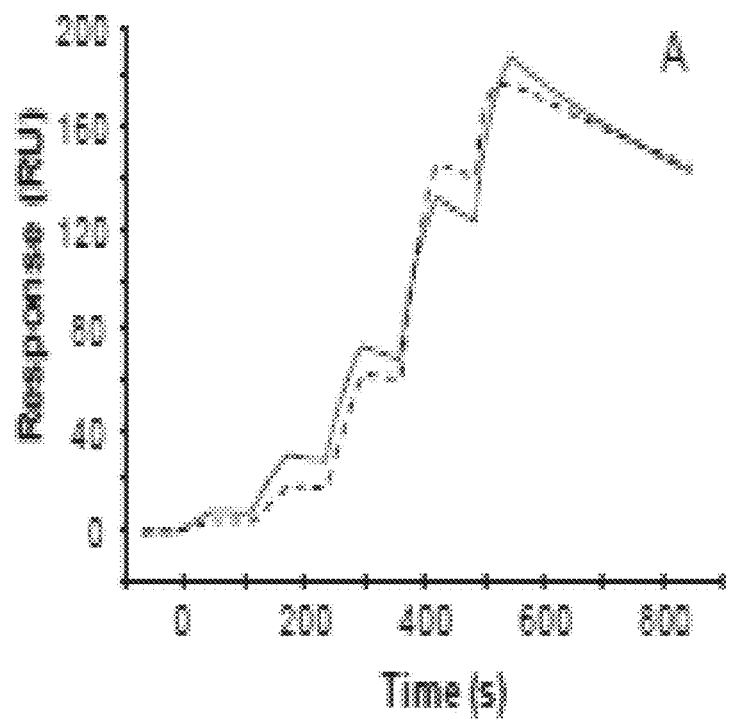
FIG. 3 shows an example of two binding curves that are difficult to fit to theoretical models
Figure 3:
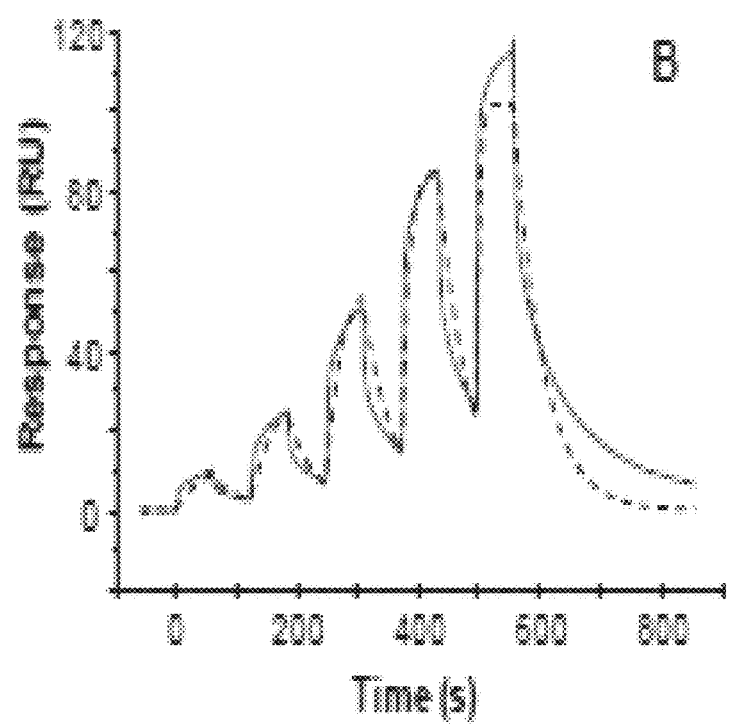

A representative binding curve (sensorgram) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Below the horizontal axis, the acquisition cycle for acquiring a binding curve is schematically disclosed divided in different time sections where the sensor surface is put into contact with different fluids. Initially, from $t_1$ to $t_2$, buffer (B) is passed over the sensing surface giving the baseline response I in the binding curve. Then, during from $t_2$ to $t_3$, the sensor surface is contacted with a sample containing an analyte at a concentration $C_1$ whereby an increase in signal is observed due to binding of the analyte. This part II of the binding curve is usually referred to as the "association phase". Eventually, a steady state condition is reached at or near the end of the association phase where the resonance signal plateaus at III (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of the association phase, at $t_3$, the sample is often replaced with a continuous flow of buffer (B) and a decrease in signal reflects the dissociation, or release, of analyte from the surface. This part IV of the binding curve is usually referred to as the "dissociation phase". The analysis is optionally ended by a regeneration step, at V where a solution capable of removing bound analyte from the surface (R), while (ideally) maintaining the activity of the ligand, is injected over the sensor surface. This is indicated in part V of the sensorgram. At $t_5$ injection of buffer (B) restores the baseline I and the surface is now ready for a new analysis. In some situations it may be convenient to omit the regeneration step V and initiate a new injection cycle without regeneration. Examples of such situations comprise concentration series of the same analyte, screening of analytes with a sufficiently high dissociation rate to allow essentially complete dissociation, etc.

From the profiles of the association and dissociation phases II and IV, respectively, information regarding the binding and dissociation kinetics is obtained, and the height of the binding curve at III represents affinity (the response resulting from an interaction being related to the change in mass concentration on the surface).

THE INVENTION

It is to be understood that the invention is not limited to the particular embodiments of the invention described above, but the scope of the invention will be established by the appended claims.

As mentioned the present invention relates to a method and a biosensor system for evaluation of an interaction between an analyte in a fluid sample and a ligand immobilized on a sensor surface of a biosensor. The biosensor may be based on any type of affinity-based detection method where an analyte binds to a ligand immobilised on a sensing surface, provided that a change at the sensing surface can be measured which is quantitatively indicative of binding of the analyte to the immobilised ligand thereon. According to one embodiment, schematically disclosed in FIG. 4, the method comprises the steps of:
  providing a reference binding curve 10, representing a reference interaction for a predetermined acquisition cycle,
  acquiring, using the biosensor, a sample binding curve 20 for the analyte ligand interaction for the predetermined acquisition cycle,
  registering the deviation of the sample binding curve from the reference binding curve 40, and
  classifying the analyte ligand interaction 50 as equivalent to the reference interaction when the registered deviation is less than a predetermined deviation criteria.

Figure 4:
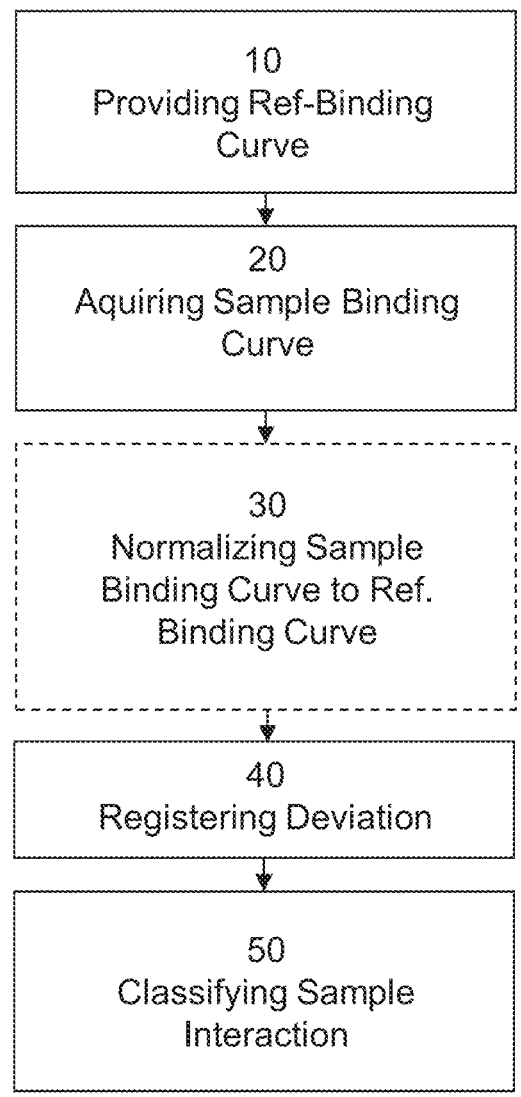
FIG. 4 shows a schematic block diagram of a method according to one embodiment of the present invention.

As indicated by the dashed box in FIG. 4, the method may optionally comprise the step of normalizing the sample binding curve with respect to the reference binding curve 30 before the deviation is registered. Such normalization may be used to compensate for variations in ligand activity on the sensor surface.

Throughout this disclosure, the term reference binding curve refers to a binding curve that is characteristic for a reference interaction such as:
  an interaction between a specific analyte-ligand pair,
  a particular interaction type that may be common to a group of two or more analyte-ligand pairs,
  a particular interaction behaviour indicative of a specific interaction mechanism,
  a etc.

The reference binding curve may be provided in essentially any suitable way, and it may be a direct binding curve for a particular interaction that is used directly as acquired using a biosensor or it may be a refined binding curve that is provided by manipulating one or more binding curves as will be disclosed more in detail. In one embodiment the reference binding curve is provided by acquiring, using the biosensor, one or more binding curves for a reference-analyte ligand interaction at the predetermined acquisition conditions. In some embodiments, the reference binding curve may be a theoretical binding curve that is not based directly on a binding curve acquired by a biosensor, but based on a theoretical or empirical model, e.g. a binding curve that is specifically designed to characterize a specific interaction mechanism or the like. A theoretical binding curve may e.g. be simulated using a theoretical model and appropriate kinetic and affinity constants.

In the present method, the reference binding curve is representative for the reference interaction for a predetermined acquisition cycle, and the sample binding curve for the analyte ligand interaction to be evaluated is acquired using the same predetermined acquisition cycle, whereby the resulting binding curves may be evaluated by a direct comparison instead of fitting the response to a theoretical model or the like to extract specific interaction parameters for evaluation.

Throughout this disclosure, the term predetermined acquisition cycle comprises the collective steps and settings of the biosensor as well as the concentration of the analyte in the sample fluid(s), which have influence on the shape of a binding curve registered with the biosensor. According to one embodiment, the predetermined acquisition cycle comprises at least one association phase wherein the sensor surface is put into contact with a fluid sample comprising analyte at a predetermined concentration. In one embodiment the predetermined acquisition cycle comprises at least two association phases for different analyte concentrations, whereby the contribution from kinetic characteristics of the analyte ligand interaction increases in the resulting binding curve. The predetermined acquisition cycle may comprise at least one dissociation phase wherein the sensor surface is put into contact with a fluid free from analyte. FIG. 5 shows an example of a predetermined acquisition cycle and an example of a reference curve comprising 5 association phases for analyte concentrations $C_1$ to $C_5$ with intermediate dissociation phases B wherein the sensor surface is put in contact with a buffer free from analyte. In FIG. 5 the acquisition cycle is illustrated by a process timeline divided into different sections at specified timepoints $t_n$. As can be seen from the associated reference binding curve, $C_1<C_2<C_3<C_4<C_5$. However it should be noted that the predetermined acquisition cycle in no way should be limited to the example of FIG. 5, and a predetermined acquisition cycle may be designed in any suitable way to facilitate the evaluation and classification of the analyte ligand interaction. The predetermined acquisition cycle may e.g. comprise:
- one single association phase with analyte concentration $C_1$,
- several association phases at the same analyte concentration $C_1$,
- two or more consecutive association phases with no intermediate dissociation phase,
- one or more regeneration phases,
- a high analyte concentration followed by a lower analyte concentration,
- passing the same analyte over two or more biosensor surfaces with different ligands immobilized thereon, e.g. to analyse bispecific and multispecific binders such as antibodies or the like,
- competition type assays,
- . . . .

Some parameters defined by the predetermined acquisition cycle may be related to the type of biosensor that is used and to settings of the same. For example, when the sensor surface of the biosensor is provided in a flow cell, then the predetermined acquisition cycle may also define the flow rate of fluid through the flow cell, as the association and dissociation rates under some conditions are dependent on the flow rate. Other parameters that may be relevant are the temperature at the biosensor, attenuation of ligand activity, etc.

The analyte concentrations $C_1$ to $C_5$ may be prepared off line and provided in separate sample containers or the concentrations may be provided by an in line mixing unit capable of mixing a sample stock solution at high concentration with buffer or the like to a sample fluid with the predetermined concentration of analyte.

Figure 5A:
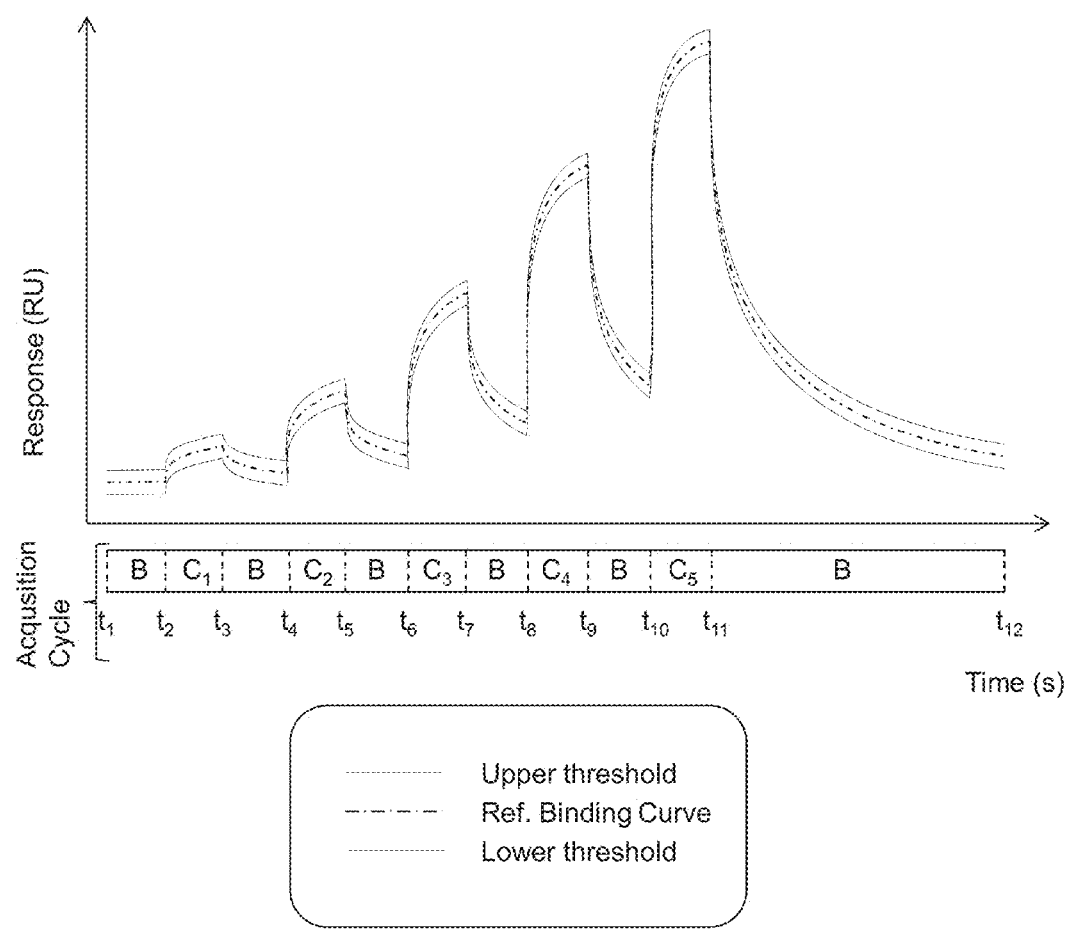
FIGS. 5 to 9 illustrates one embodiment of the present invention.

In FIG. 5a the reference binding curve is displayed as a dashed curve indicative of the reference interaction against which, the analyte ligand interaction will be evaluated. According to one embodiment the step 40 of registering the deviation of the sample binding curve from the reference binding curve is performed by a direct calculation of the deviation from the reference binding curve, and whereby a direct threshold with respect to the amount of deviation may be set for the step of classification 50. According to other embodiments, more specific threshold criteria may be provided for the step of classification, e.g. by weighting of deviation with respect to one or more phase or part thereof in the predetermined acquisition cycle, or the like.

Figure 5B:
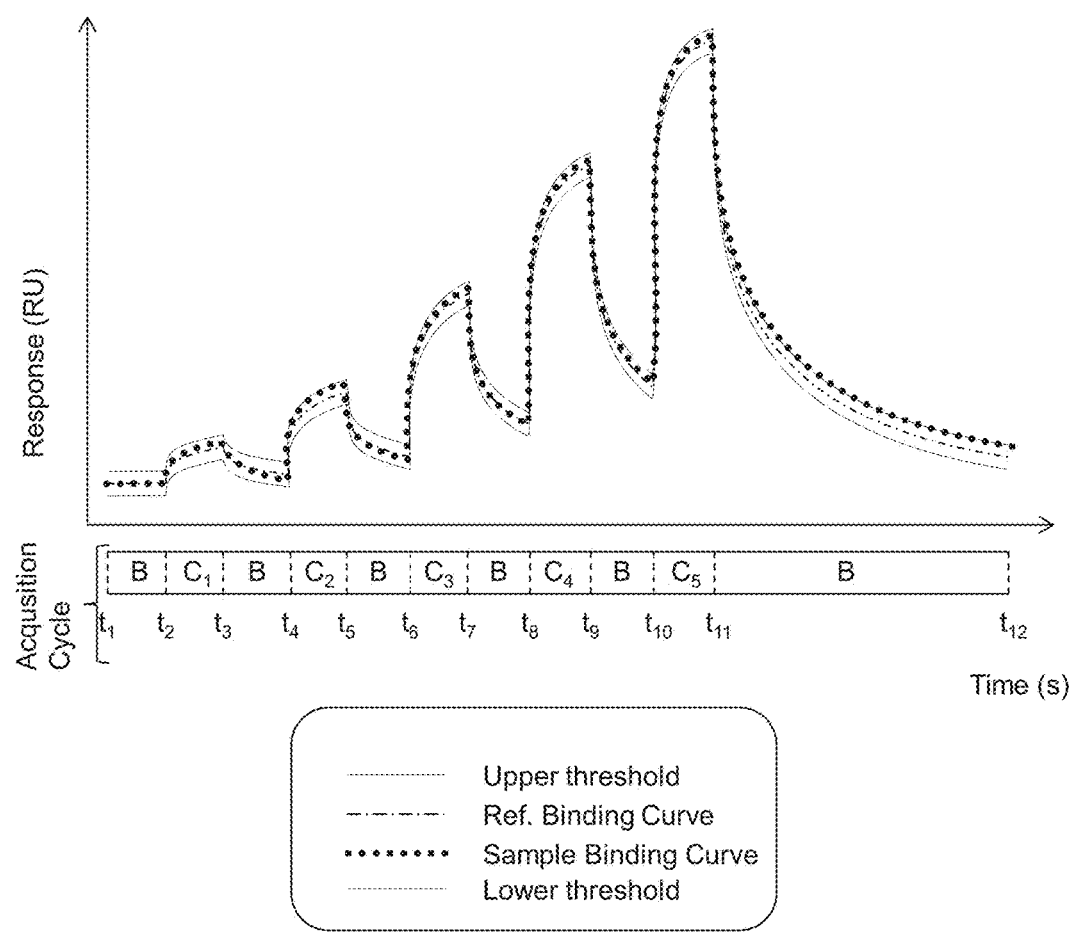

According to one embodiment, as schematically shown in FIG. 5a, an upper and/or a lower reference threshold curve may be provided as to define acceptance thresholds with respect to the reference binding curve, and wherein the deviation criteria is defined with respect to the reference threshold curve(s). In FIG. 5a the upper and/or a lower reference threshold curves are disclosed as thin solid lines, and they each represent a linear shift of the reference binding curve along the y axis in the positive and negative direction respectively i.e.:
Upper threshold curve=reference binding curve+predetermined upper threshold parameter
Lower threshold curve=reference binding curve−predetermined lower threshold parameter FIG. 5b the acquisition cycle and corresponding reference curve of FIG. 5a, wherein sample binding curve is plotted as a thick dotted line for classification. In FIG. 5b the disclosed sample binding curve falls entirely within the borders of the upper and lower threshold curves and may therefore be classified as equivalent to the reference interaction for the predetermined thresholds. According to one embodiment, the classification may be based on a single upper or lower threshold curve wherein the sample binding curve is classified as equivalent to the reference interaction when it satisfies the one threshold curve. As will be disclosed more in detail below and in association with examples, the deviation criteria in the form of upper and lower threshold curves may be provided based on statistical information calculated from capture of multiple reference binding curves. In this way, the thresholds used for classification of analyte ligand binding curves may be more representative for real interaction deviations etc. According to one embodiment, the predetermined deviation criteria for classification of the analyte ligand interaction are weighted in response to different phases or parts thereof of the predetermined acquisition cycle.

Figure 6:
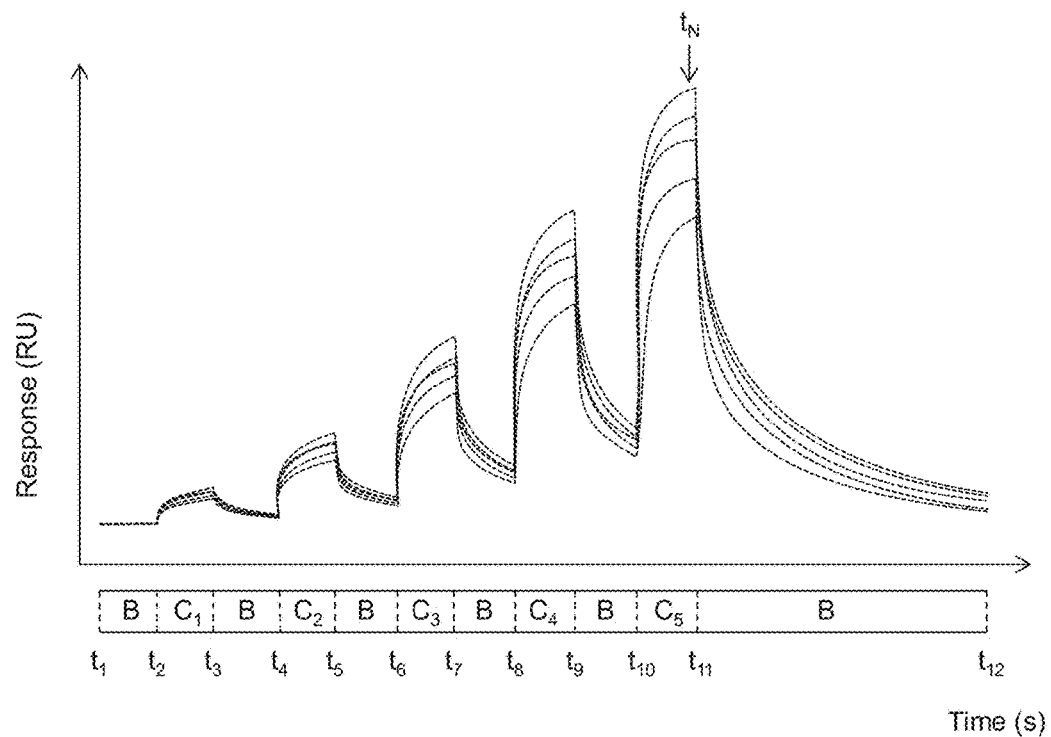
Figure 7:
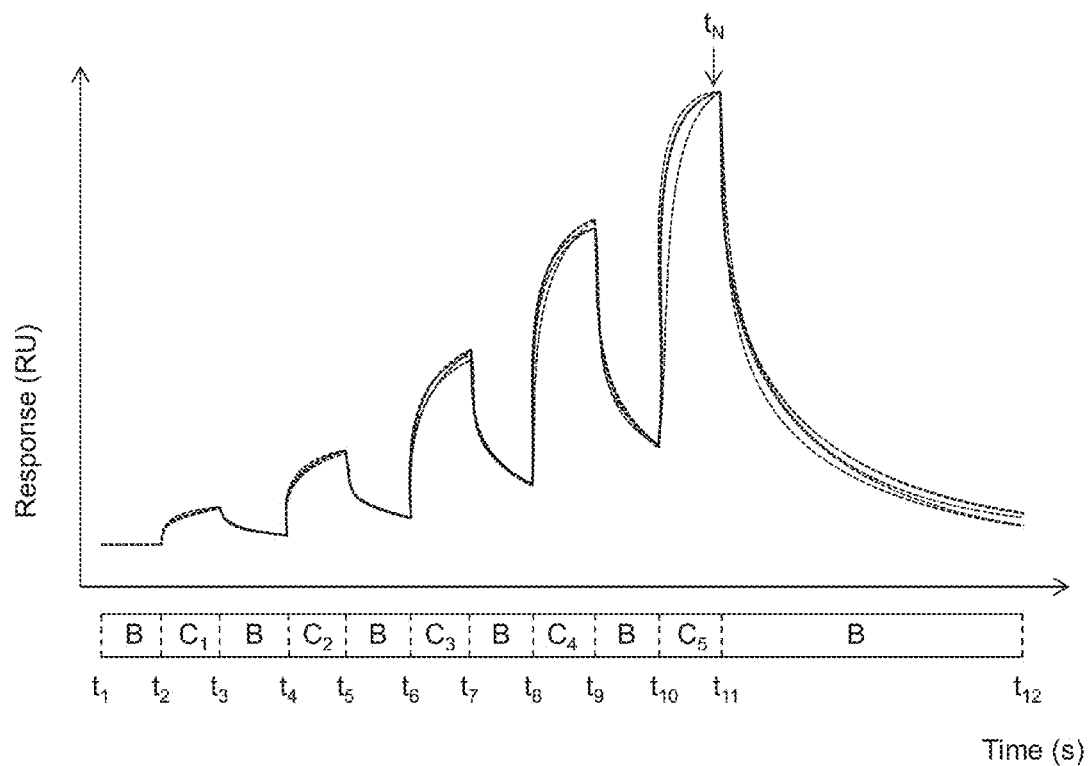

FIGS. 6 to 9 show one way of building a statistically defined reference binding curve as well as upper and lower threshold curves. In order to provide a statistically relevant reference binding curve, two or more binding curves are acquired for a reference-analyte ligand interaction for the predetermined acquisition cycle. In FIG. 6, five reference-analyte ligand interaction binding curves are schematically disclosed for the predetermined acquisition cycle. Due to variations in biosensor response and sample preparation etc. a certain amount of deviation between the reference-analyte ligand interaction binding curves may be expected, and therefore the evaluation in accordance with the present method may be arranged to take such deviations into account. According to one embodiment, the reference binding curve is then defined as the average or the median curve of said two or more binding curves and the deviation of the sample binding curve is registered with respect to the average or median curve in step 40. For some reference-analyte ligand interactions, the deviation between the registered binding curves is characterized by a deviation/attenuation type pattern. In such cases the reference-analyte ligand interaction binding curves may be normalized before calculation of a statistically defined reference binding curve. Normalization may be performed in any suitable way in accordance with the specific deviation/attenuation pattern, and according to one embodiment it may be performed by selecting a suitable point of normalization $t_N$ in the predetermined acquisition cycle and rescaling the reference-analyte ligand interaction binding curves in the y-direction so that all curves have the same value at said point $t_N$. The point of normalization is preferably selected in accordance with the predetermined acquisition cycle, and in one embodiment it is selected as a point a short time frame before the end of the association phase with highest response. FIG. 7 schematically discloses the reference-analyte ligand interaction binding curves of FIG. 6 normalized with respect to the point of normalization $t_N$. Another example is to select two or more points of normalization $t_N$ and to normalize the curves e.g. based on the average response at said points of normalization $t_N$.

Figure 8:
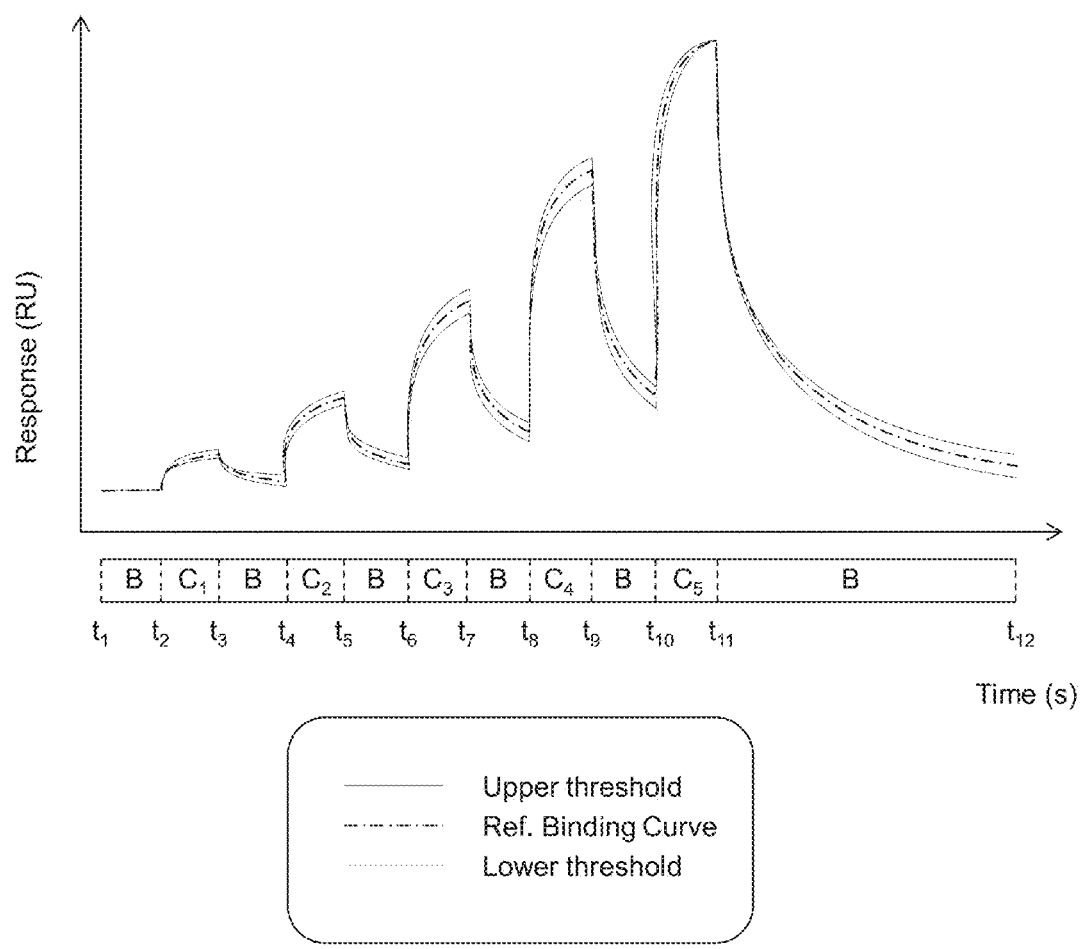

In FIG. 8 the reference binding curve is schematically illustrated as an average curve based on the normalized reference-analyte ligand interaction binding curves in FIG. 7. Alternatively, the reference binding curve could be provided as the median curve or in any other suitable statistical approach that would provide a reference binding curve representing the reference interaction for the predetermined acquisition cycle. By using a statistical approach for defining the reference binding curve, it also provides information about the deviation from e.g. the average curve, and such information may be used in order to provide reference threshold curves that e.g. allows a wider threshold range with respect to one or more phase or part thereof in the predetermined acquisition cycle where the registered reference-analyte ligand interaction binding curves showed a wider range of deviation. In one embodiment the upper and lower reference threshold curves are defined by the mm and max of said two or more reference-analyte ligand interaction binding curves respectively. In one embodiment, the upper and lower reference threshold curves are defined by selecting a predetermined percentage deviation from the reference binding curve or the like. In one embodiment, the upper and lower reference threshold curves may be defined by a theoretical simulation using appropriate kinetic and affinity constants reference binding curve or the like. In one embodiment, the upper and lower reference threshold curves are may be manipulated by a user through a graphical user interface or the like, the user may e.g. be able to do one or more of:

Move one or more of the threshold curves with respect to the reference curve. The movement may be free or restricted to preserve alignment to the reference curve.

Draw custom threshold curves using drawings tools.

Modify existing threshold curves using drawings tools or the like.

Figure 14:
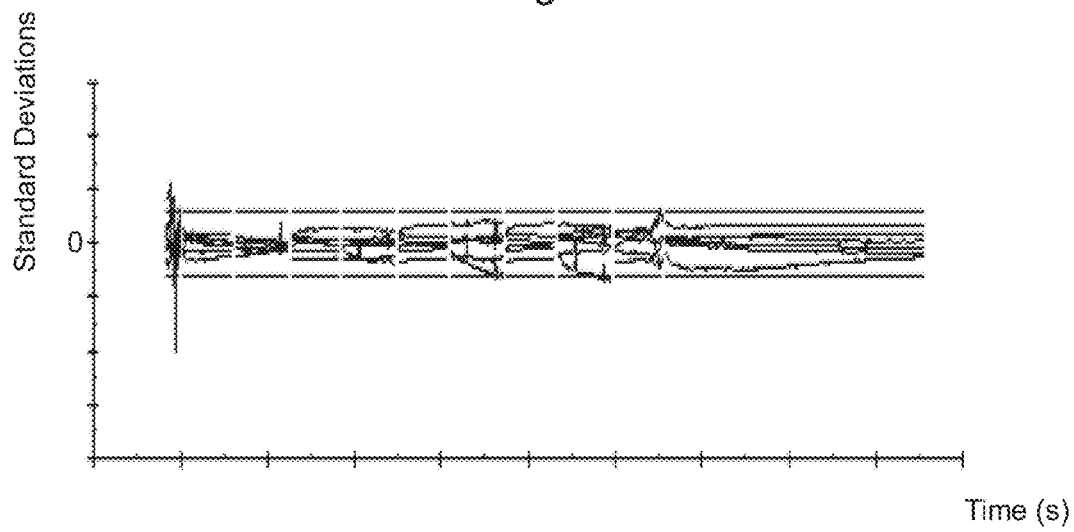

In one embodiment, which is schematically disclosed in FIG. 8 and will be disclosed in further detail in the examples, the upper and lower reference threshold curves are defined by a predetermined standard deviation from the average curve. By using the concept of standard deviation, the relevance of the evaluation can be established to a high level of certainty. The concept of using standard deviation to define thresholds for the evaluation in accordance with the present invention further makes it possible to present evaluation results in the form of a standard deviation plot to clearly illustrate the fit of a sample binding curve to the defined reference threshold curves, as is illustrated in FIG. 14 with reference to example 1. According to one embodiment, the method comprises the step of:

displaying on a graphical display, for visual inspection, one or more of:

an overlay plot of the reference binding curve, one or more sample binding curves and optionally the upper threshold curve, the lower reference threshold curve and the control binding curve, a deviation plot wherein registered deviation from the reference binding curve is displayed for one or more sample binding curves, and a reference threshold curve plot wherein one or more sample binding curves are displayed on a reference threshold scale.

Further, as already mentioned, the sample binding curve(s) may be normalized with respect to the reference binding curve in order to avoid influence from e.g. biosensor fluctuations and the like. Moreover, in order to verify the function of the biosensor and the involved analyte ligand interaction is relevant, the method may comprise the steps of:

acquiring, in association with the sample binding curve, a control binding curve for a control-analyte ligand interaction, registering the deviation of the control binding curve from the reference binding curve, and verifying the acquisition of the sample binding curve when the deviation of the control binding curve is less than a predetermined control limit.

Like above, the control binding curve may also be normalized with respect to the reference binding curve. In one embodiment, the predetermined control limit may be the same as the reference threshold curves. The control-analyte ligand interaction may conveniently be the same as the reference interaction.

According to one embodiment, the step of classifying the analyte ligand interaction comprises the step of calculating the percentage of data points of a sample binding curve that are located outside the reference threshold curves and wherein the deviation criteria is the maximum percentage of data points allowed to be outside of the reference threshold curves. According to one embodiment, the step of classifying the analyte ligand interaction comprises the step of calculating the sum of squares for the threshold reference binding curve and/or sample binding curve where the reference curve have first been subtracted and wherein the deviation criteria is the maximum sum of squares allowed. According to one embodiment the step of classifying comprises calculation of a similarity score based on the percentage of points identified to be inside the threshold curves and the calculated sum of square ratio between limit and sample distances for points outside threshold curves. Hence the similarity score equals the percentage of points inside plus the percentage of points outside multiplied by the SSQ (limit distances) divided by the SSQ (sample distances). In this embodiment points inside are given the value 100 and points outside are scaled based on the distances to the reference curve.

Figure 9:
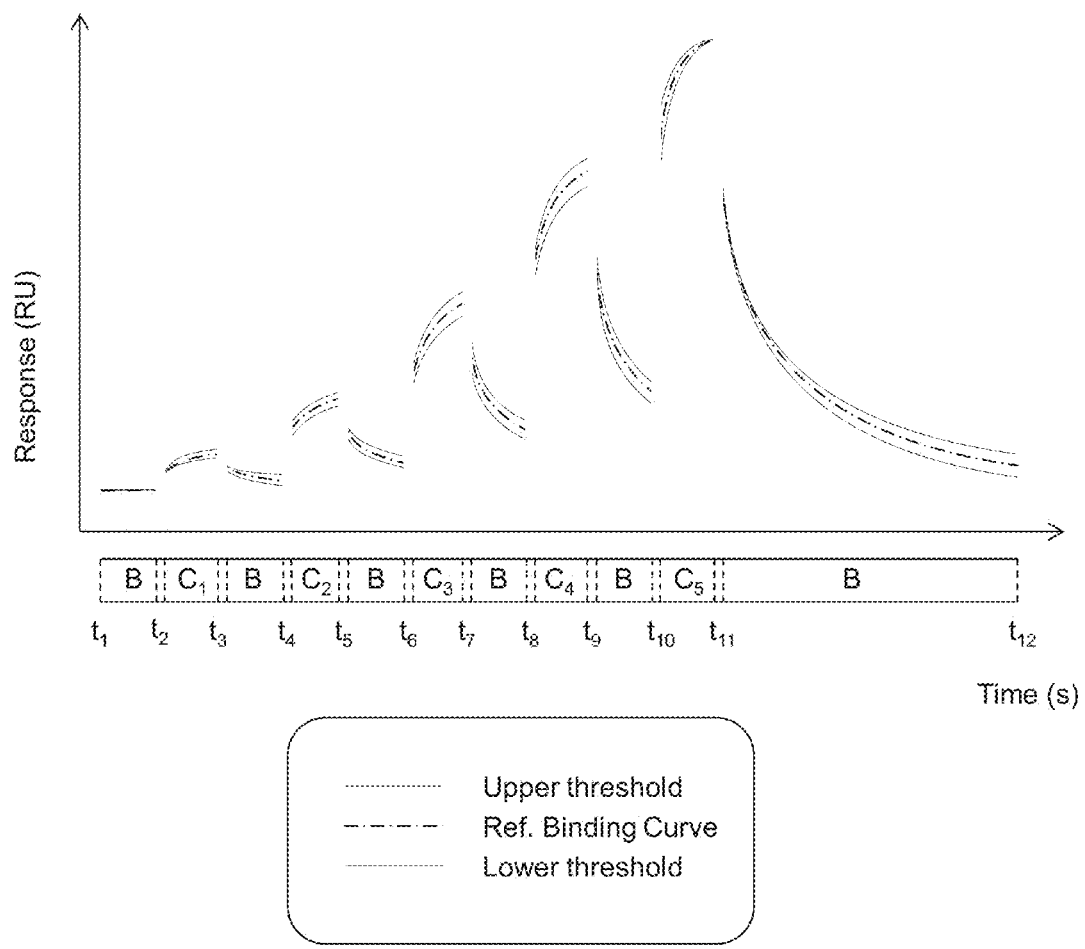

In one embodiment, schematically disclosed in FIG. 9, the current method comprises the step of excluding one or more sections of the binding curves from the step of registering deviation and following steps. The exclusion of one or more sections from the binding curves may be useful to exclude regions that comprise disturbances like spikes or the like. In one embodiment, the method includes a step of identifying disturbances to automatically exclude such sections. In one embodiment, the sections to be excluded are predetermined based on prior knowledge of the analyte ligand interaction and the predetermined acquisition conditions, and in the embodiment disclosed in FIG. 9, the excluded sections comprise transitions between association and dissociation phases as defined by the predetermined acquisition cycle.

The method according to may be used to evaluate any interaction between an analyte in a fluid sample and a ligand immobilized on a sensor surface of a biosensor wherein it is possible to provide a relevant reference binding curve, representing a reference interaction, and where quick and reliable relative evaluation is desired. Examples of application areas comprise:

process quality control, whereby the method is used to verify final or intermediate process results, screening of analyte/ligand libraries to identify a certain type of binding behaviour or the like, e.g. fragment screening, off-rate screening thermodynamic screening, screening for monophasic binders, potency assays in combination with calibration free concentration analysis CFCA, wherein evaluation of response curves ensure similarity for target/receptor binding which is the basis for a potency assay.

According to one embodiment, at least one of the ligand and analyte is selected from the group of: drug targets and natural their binding partners or reagents used to characterize drug targets.

According to one embodiment, there is provided a biosensor system arranged to perform the method according to above. The biosensor system, may e.g. be a SPR based system like the Biacore® systems or e.g a waveguide interferometer like the ForteBio® systems or the like. Still further, there is provided a computer program arranged to, when run on a computer, control the operation of a biosensor system to perform the method according above.

Example 1

Figure 10:
FIGS. 10 to 17 illustrates Example 1.
Figure 11:
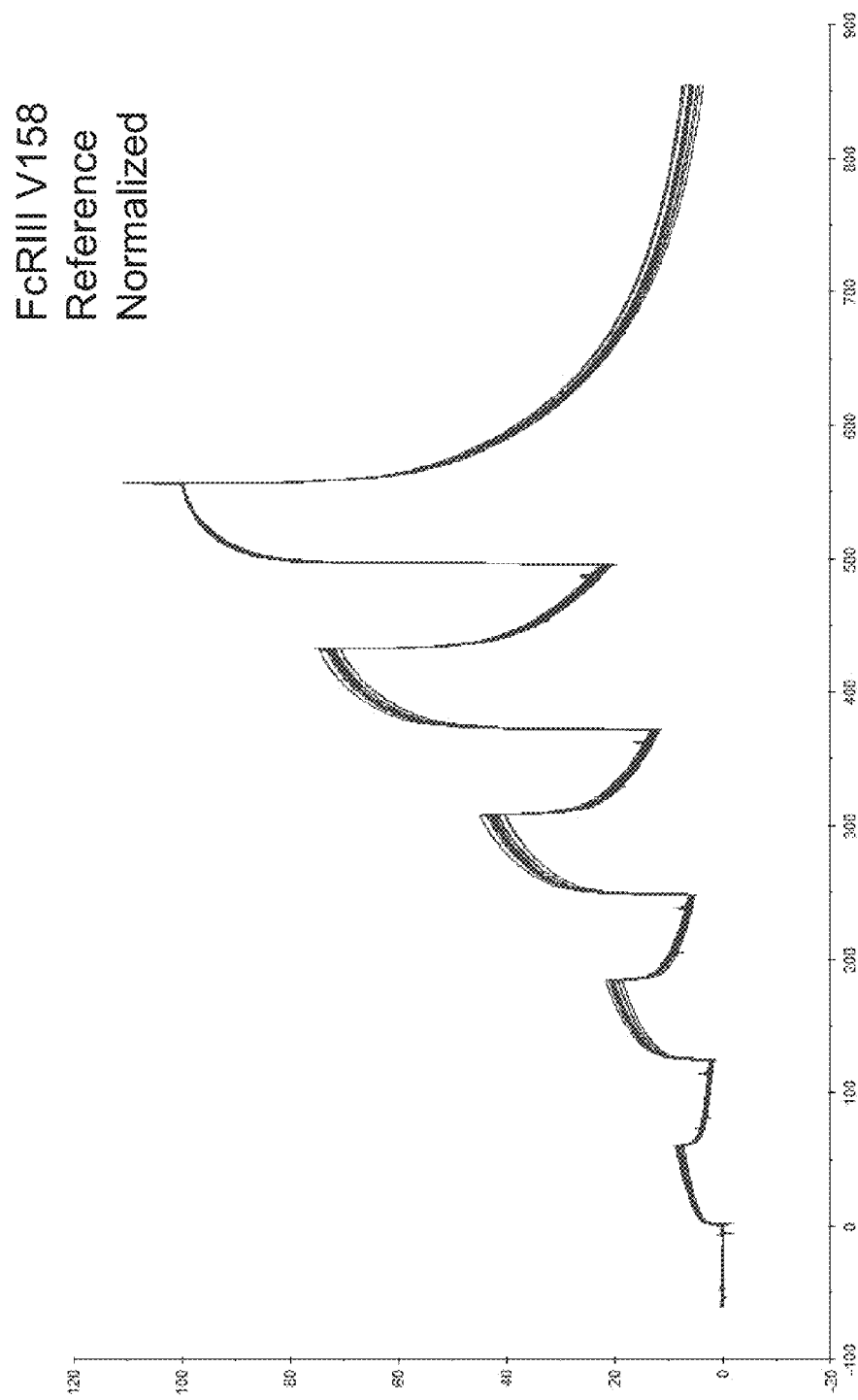

FIGS. 10 to 17 shows one example of evaluation of an interaction between an analyte in a fluid sample and a ligand immobilized on a sensor surface of a biosensor in accordance with one embodiment of the present invention. In this example a his tagged Fc receptor, FcγRIIIaVal158, was captured on an anti-histidine biosensor surface and the binding of an antibody, Rituximab, to the biosensor surface was registered. FIG. 10 shows a range of reference binding curves collected for the interaction for an acquisition cycle with 5 association phases at increasing antibody concentration, each with a subsequent dissociation phase. It can be seen that there is a large variation in response between different reference binding curves. FIG. 11 discloses the reference binding curves normalized using data a few seconds before the end of the last association phase as basis for normalization.

Figure 12:
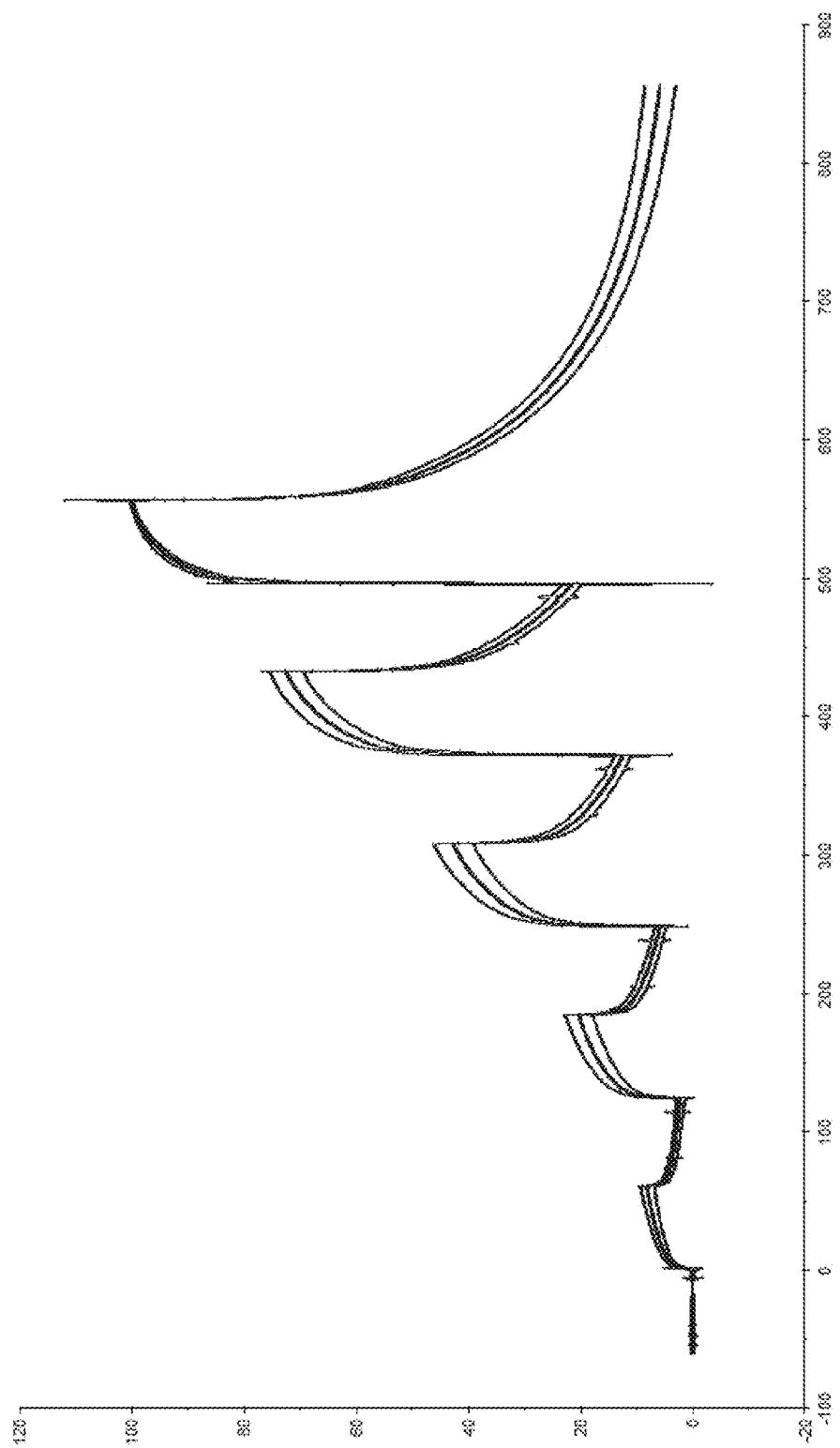
Figure 13:
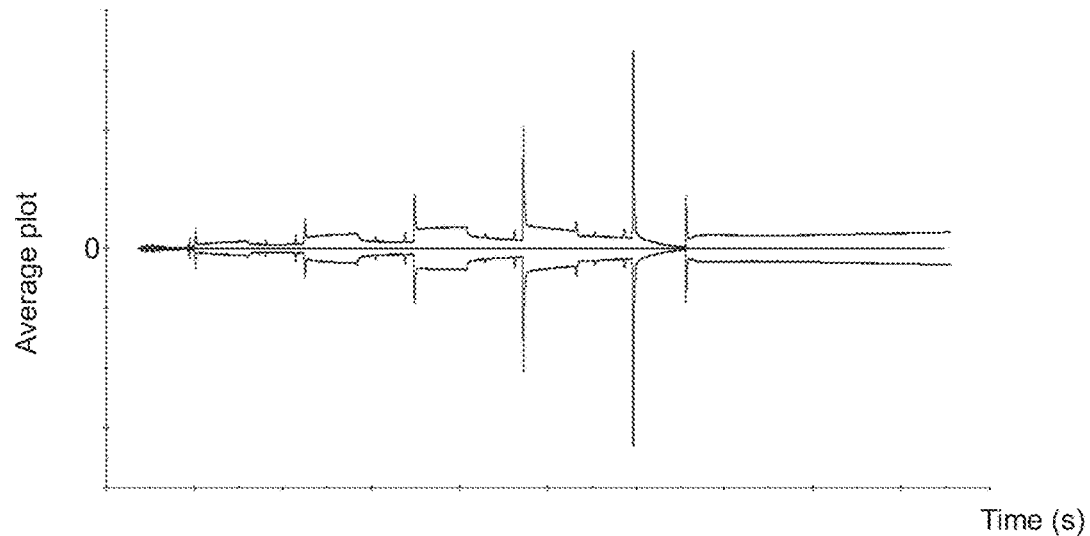

In FIG. 12 the middle curve represents the average of the normalized reference binding curves of FIG. 11 and the upper and lower curves represents average +/− three standard deviations, respectively. FIG. 13 shows the corresponding difference plot between the average reference binding curve and the upper and lower curves clearly showing where there are uncertainties in the registered reference binding curves, whereas FIG. 14 shows the registered reference binding curves replotted on a standard deviation scale.

Figure 15:
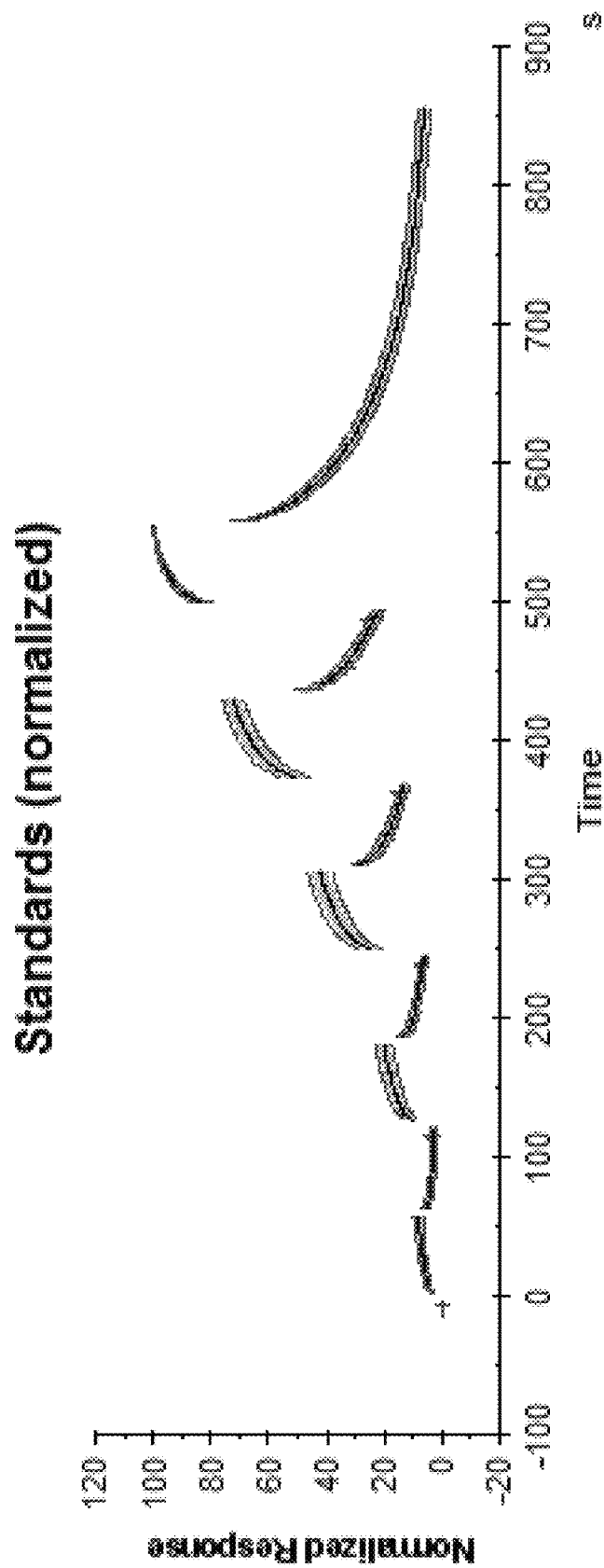
Figure 16:
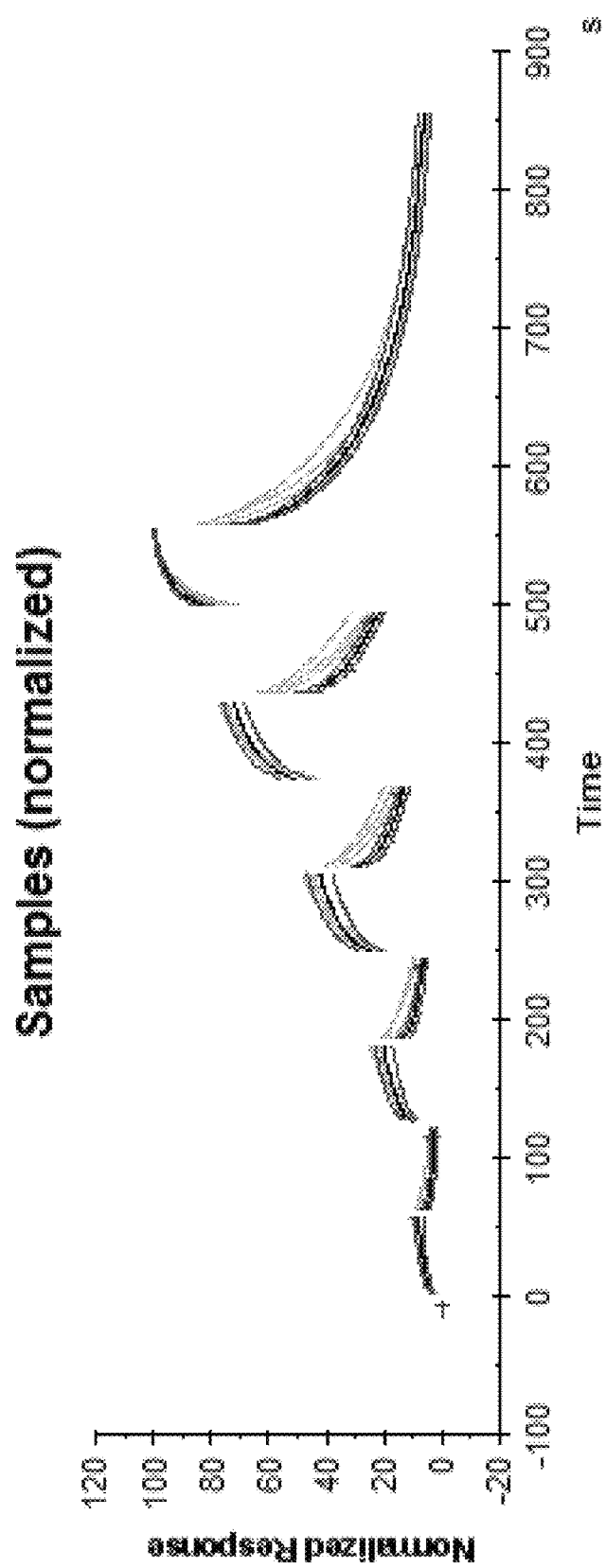
Figure 17:
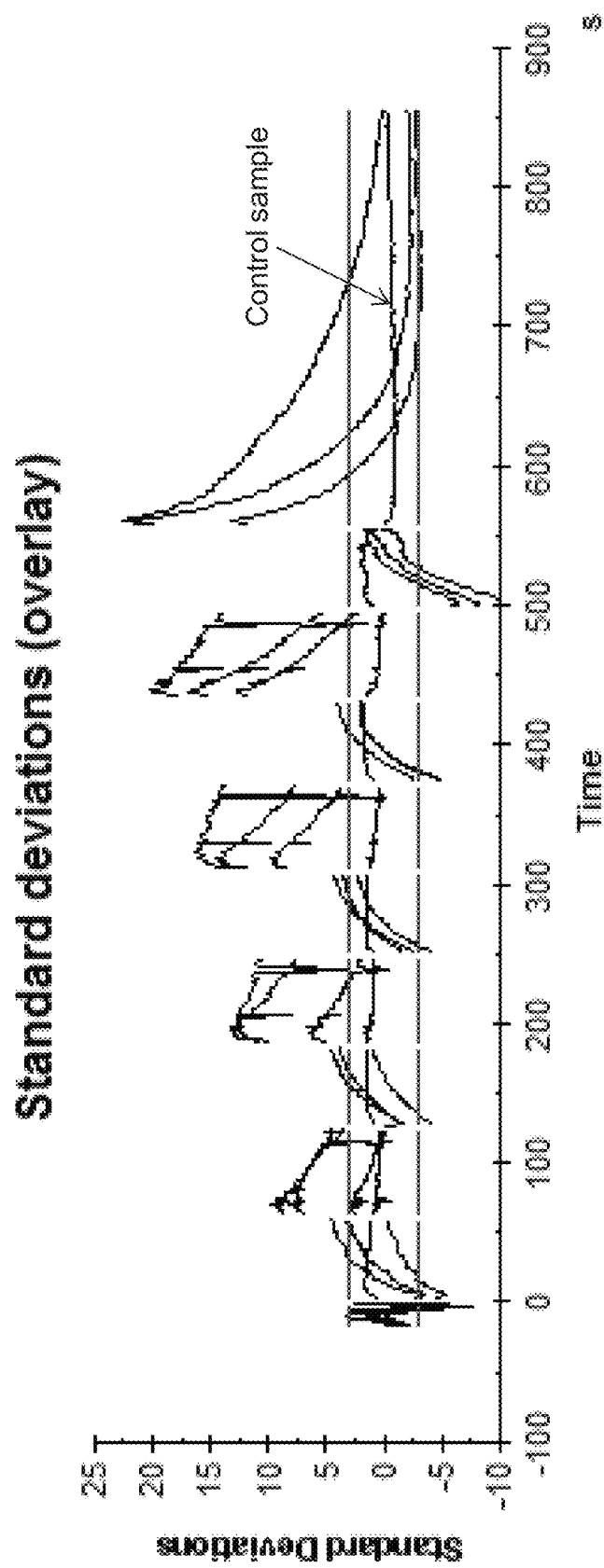

FIG. 15 shows the average and standard deviation curves with certain sections at the transitions between association and dissociation phases excluded in order to reduce the impact of uncertainties in those segments. FIG. 16 shows sample binding curves plotted in the reference binding curve plot of FIG. 15, as can be seen, not all data fall within the +/− three standard deviation curves. FIG. 17 shows the sample binding curves replotted on a standard deviation scale, and it can be seen that the sample binding curves clearly deviate more than three standard deviations from the reference binding curve at several points in time. However, a control sample registered for the interaction is concluded to behave as expected and is well within three standard deviations from the reference binding curve at all timepoints.

Example 2

Figure 18A:
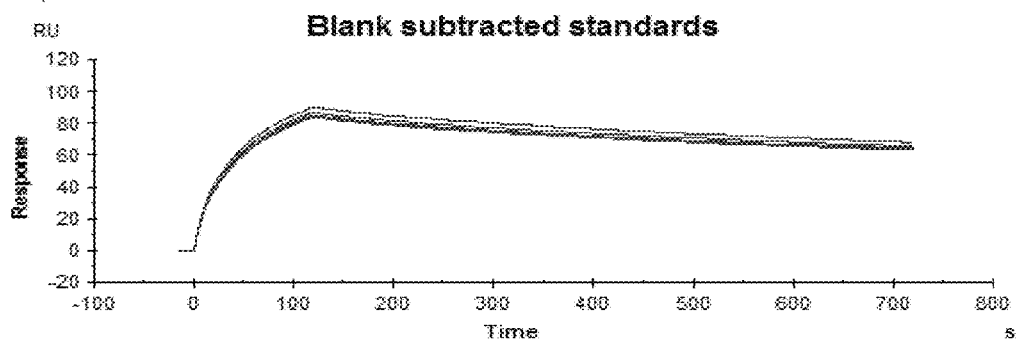
FIGS. 18 to 20 illustrates Example 2.
Figure 18B:
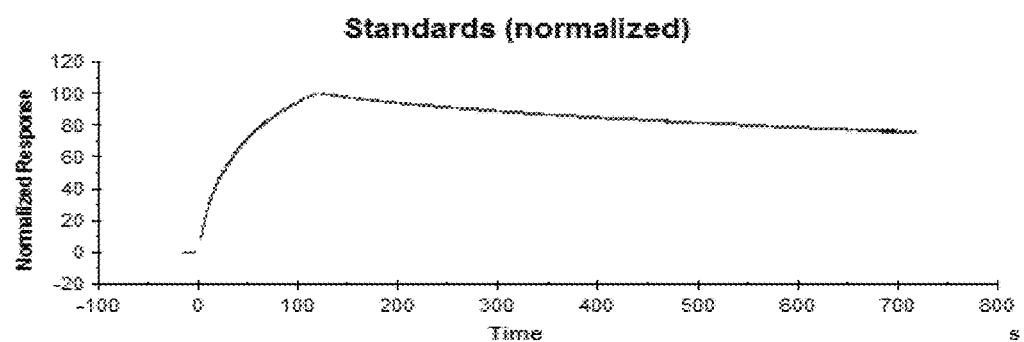
Figure 18C:
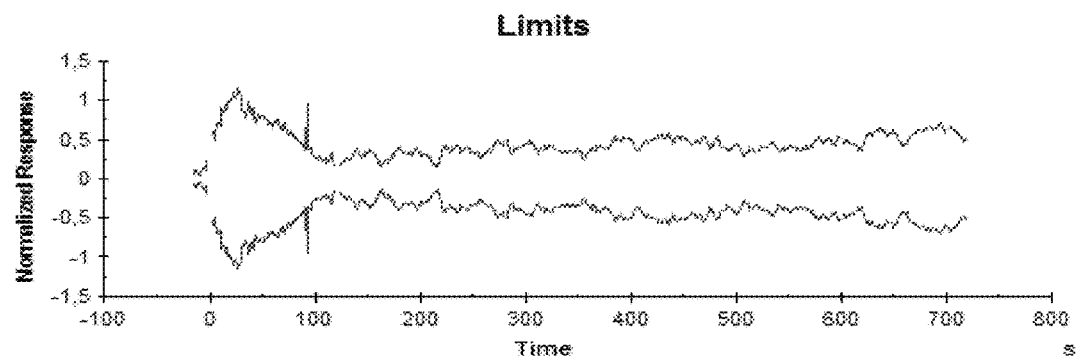
Figure 19A:
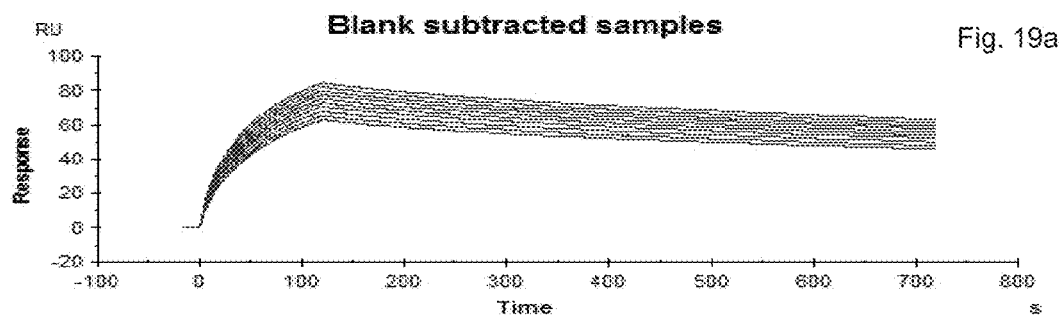
Figure 19B:
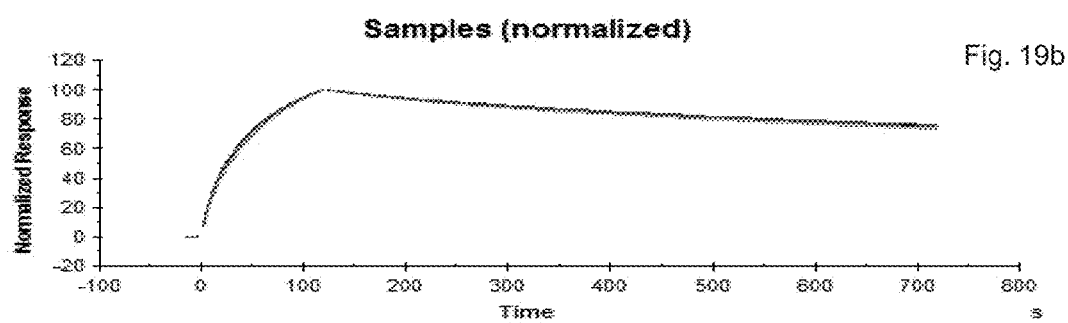
Figure 19C:
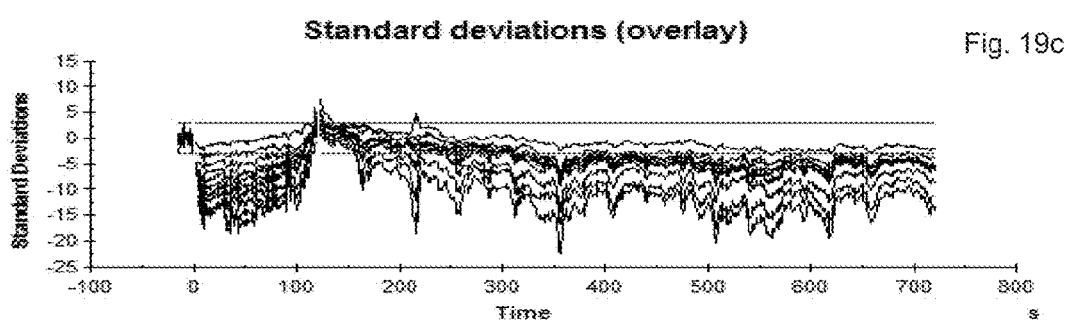
Figure 19D:
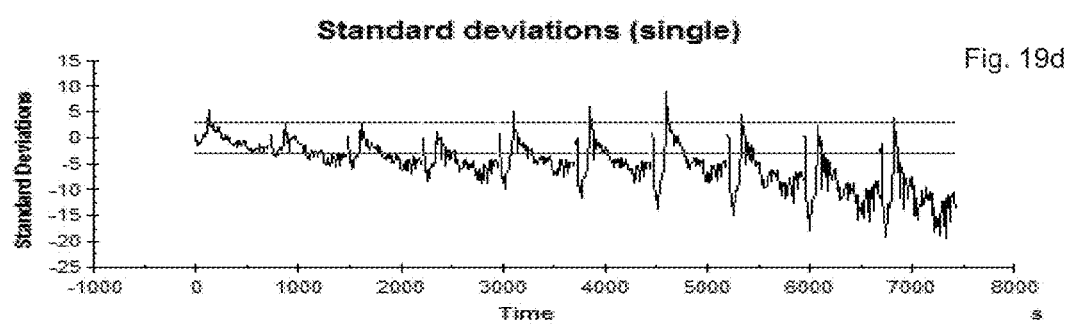
Figure 20A:
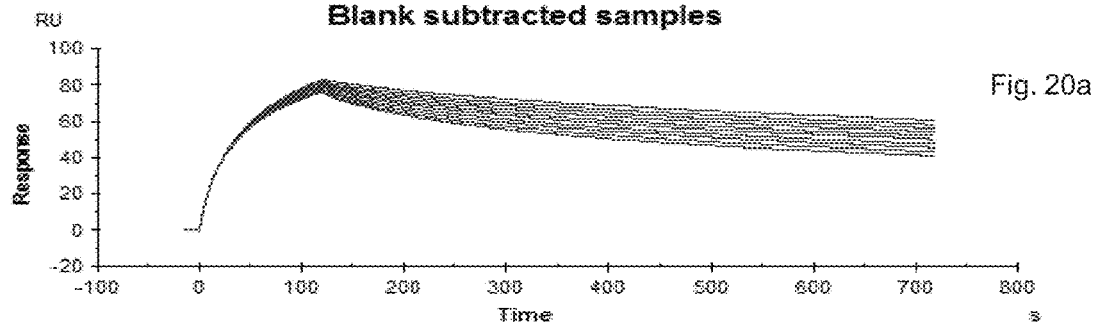
Figure 20B:
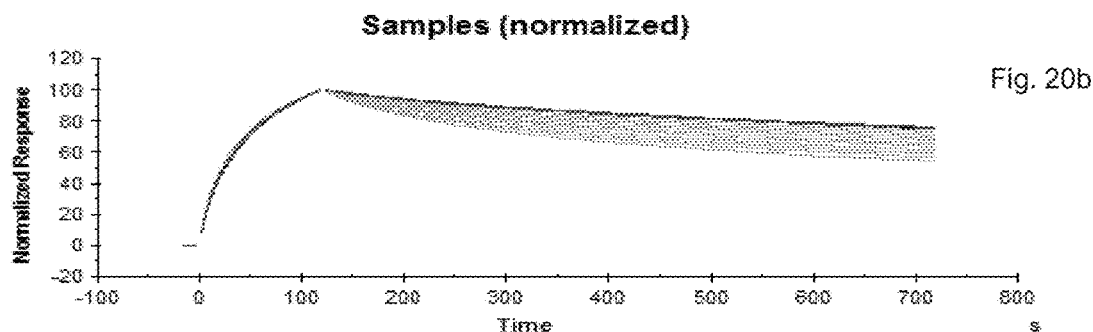
Figure 20C:
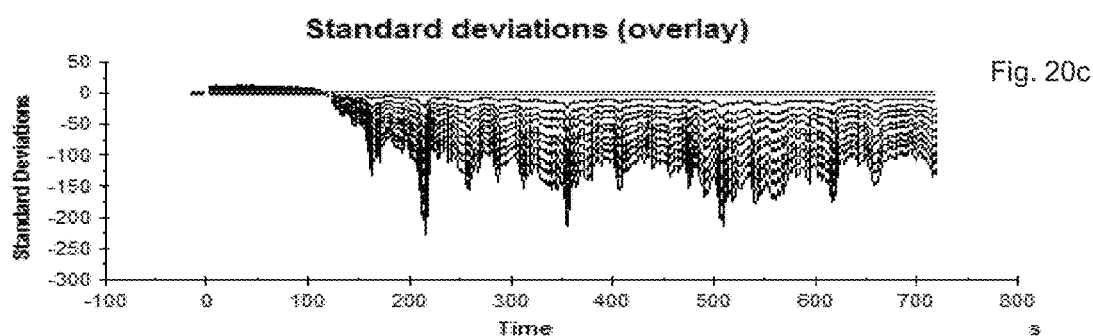
Figure 20D:
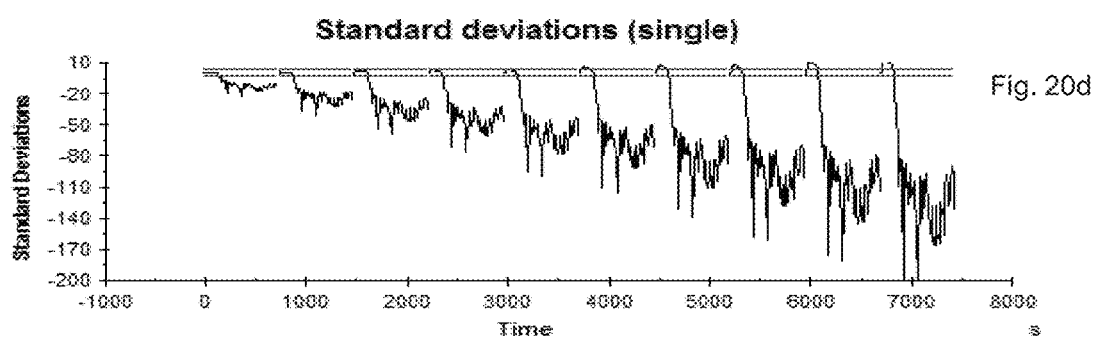

FIGS. 18 to 20 discloses an example wherein MabX-ECR reagent 3154 is evaluated in accordance with the present invention. In this example MabX-ECR reagent 3154 comprising increasing levels of stressed MabX are evaluated. FIG. 18a shows a range of reference binding curves collected for the interaction of wild type MabX-ECR reagent 3154 for an acquisition cycle with one association phase and a subsequent dissociation phase. It can be seen that there is a moderate variation in response between different reference binding curves. FIG. 18b discloses the normalized reference binding curves and FIG. 18c show the corresponding SD limit curves.

FIGS. 19 to 20 show the evaluation of increasing levels of stressed MabX, wherein FIG. 19 discloses the results achieved for pH stressed spiked MabX and FIG. 20 discloses the results achieved for Oxidized stressed MabX. In FIGS. 19 and 20, the 19a and 20a show the registered response curves after a blank run has been subtracted, 19b and 20b show the response curves following normalization, 19c and 20c show the standard deviation of each one of the registered response curves overlaid in a SD plot, and 19d and 20d show the standard deviation of the registered response curves in time succession in a SD plot. This example gives a good illustration of the intuitive evaluation provided by the present invention.

Example 3

Figure 21A:
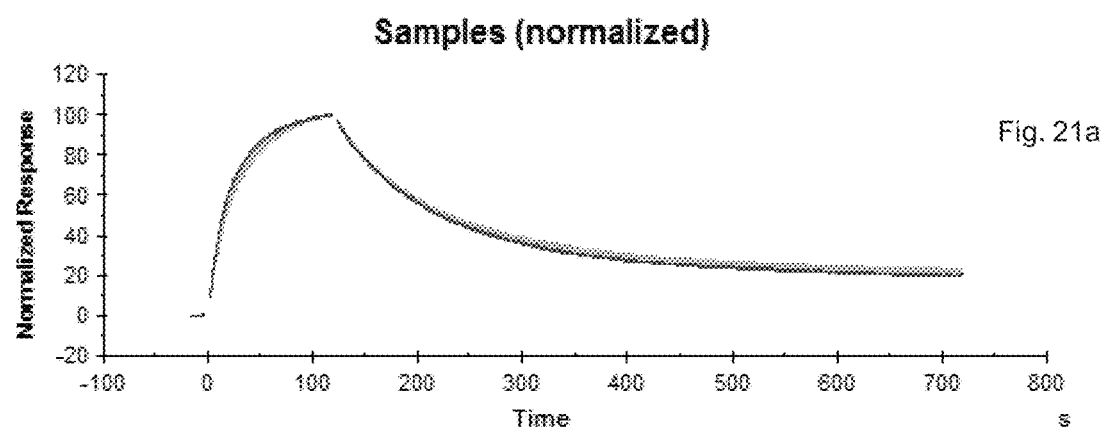
FIGS. 21 to 22 illustrates Example 3.
Figure 21B:
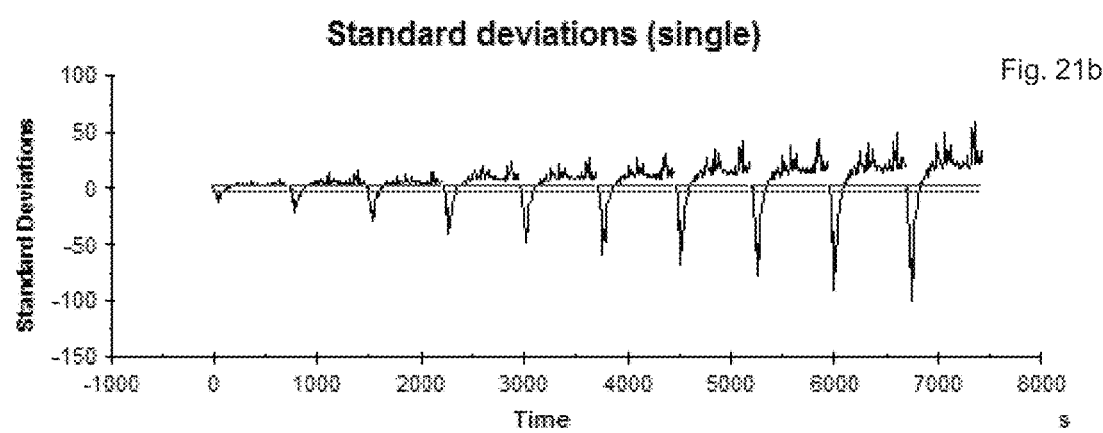
Figure 22A:
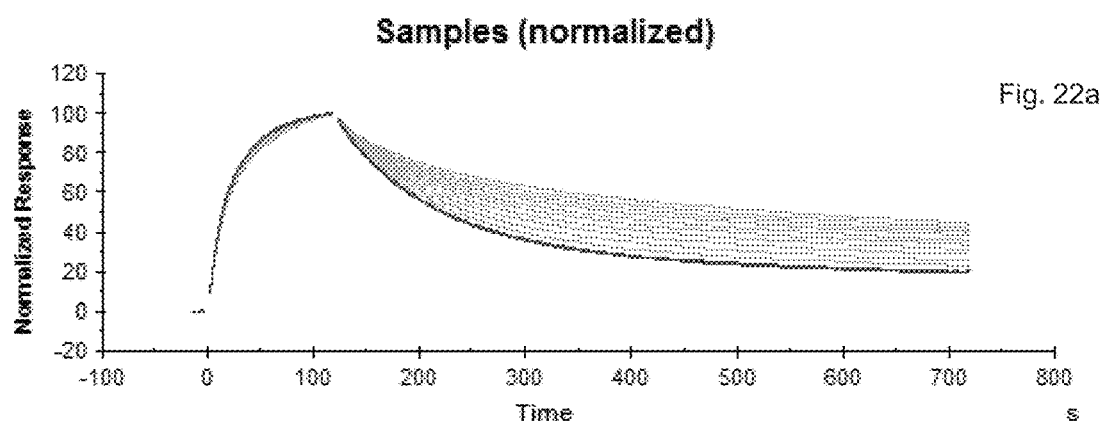
Figure 22B:
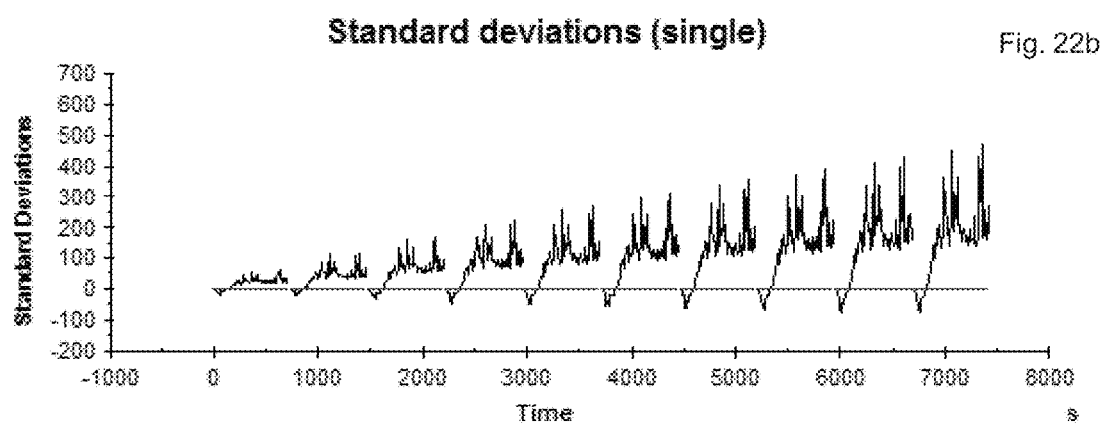

Similar to Example 2, FIGS. 21 and 22 disclose an example wherein MabX-ECR reagent 2994 is evaluated in accordance with the present invention. In this example MabX-ECR reagent 2994 comprising increasing levels of stressed MabX are evaluated. FIGS. 21 and 22 show the evaluation of increasing levels of stressed MabX, wherein FIG. 21 discloses the results achieved for pH stressed spiked MabX and FIG. 22 discloses the results achieved for Oxidized stressed MabX. In FIGS. 21 and 22, FIGS. 21a and 22a show the registered response curves following normalization, and FIGS. 21b and 22b show the standard deviation of the registered response curves in time succession in a SD plot.

The invention claimed is:

1. A method for evaluation of an interaction between an analyte in a fluid sample and a ligand immobilized on a sensor surface of a biosensor, the method comprising:
    providing a reference binding curve, representing a reference interaction for a predetermined acquisition cycle,
    acquiring, using the bio sensor, a sample binding curve for the analyte ligand interaction for the predetermined acquisition cycle,
    generating a graphical user interface, including an upper threshold curve and a lower threshold curve defined with respect to the reference binding curve, wherein at least one of the upper and lower threshold curves is movable with respect to the reference binding curve to adjust a threshold range for one or more phases in the predetermined acquisition cycle to set deviation criteria for analysis of the sample binding curve,
    excluding a section of the sample binding curve exhibiting a disturbance, wherein identification of the disturbance to automatically exclude sample binding curves with a disturbance is based on known analyte ligand interaction and predetermined acquisition conditions, wherein the exclusion contains a transition between an association phase and a dissociation phase of the predetermined acquisition cycle,
    registering a deviation of the sample binding curve from the reference binding curve according to the threshold range and deviation criteria, wherein excluded sections of the sample binding curve are not included during the registering of the deviation,
    classifying the analyte ligand interaction as equivalent to the reference interaction when the registered deviation is less than the deviation criteria, wherein the deviation criteria are weighted in response to phases of the predetermined acquisition cycle and the upper and lower reference threshold binding curves, and
    generating, based on the classification, a determination of molecular binding interaction at a sensing surface independent of interaction models, wherein the generated binding interaction excludes binding curve sections with disturbances.

2. The method according to claim 1 further including normalizing the sample binding curve with respect to the reference binding curve.

3. The method according to claim 1 wherein the reference binding curve is provided by acquiring, using the biosensor, one or more binding curves for a reference-analyte ligand interaction at the predetermined acquisition conditions.

4. The method according to claim 3 wherein two or more binding curves for a reference-analyte ligand interaction are acquired, and wherein the reference binding curve is defined as the average or the median curve of said two or more binding curves.

5. The method according to claim 4 wherein the two or more binding curves are normalized before the average or the median curve is provided.

6. The method according to claim 5 wherein the upper and lower reference threshold curves are defined by the minimum and maximum of said two or more binding curves respectively.

7. The method according to claim 5 wherein the upper and lower reference threshold curves are defined by a predetermined standard deviation from the average curve.

8. The method according to claim 1 wherein the predetermined acquisition cycle includes at least one association phase wherein the sensor surface is put into contact with a fluid sample including analyte at a predetermined concentration.

9. The method according to claim 8 wherein the predetermined acquisition cycle includes at least two consecutive association phases for different analyte concentrations.

10. The method according to claim 1 wherein the predetermined acquisition cycle includes at least one dissociation phase wherein the sensor surface is put into contact with a fluid free from analyte.

11. The method according to claim 1 wherein the sensor surface of the bio sensor is provided in a flow cell and wherein the predetermined acquisition cycle defines the flow rate of fluid through the flow cell.

12. The method according to claim 1 further including:
acquiring, in association with the sample binding curve, a control binding curve for a control-analyte ligand interaction,
normalizing the control binding curve with respect to the reference binding curve,
registering the deviation of the control binding curve from the reference binding curve, and
verifying the acquisition of the sample binding curve when the deviation of the control binding curve is less than a predetermined control limit.

13. The method according to claim 1 wherein normalization is based on the binding curve value at a point in the predetermined acquisition cycle before an end of an association phase.

14. The method according to claim 1 wherein at least one of the ligand and analyte is selected from the group of drug targets and their natural binding partners or reagents used to characterize drug targets.

15. The method according to claim 1 further including:
displaying on a graphical display, for visual inspection, one or more of:
an overlay plot of the reference binding curve, one or more sample binding curves and optionally the upper threshold curve, the lower reference threshold curve and the control binding curve,
a deviation plot wherein registered deviation from the reference binding curve is displayed for one or more sample binding curves, and
a reference threshold curve plot wherein one or more sample binding curves are displayed on a reference threshold scale.

16. The method according to claim 15 further including calculating the percentage of data points of a sample binding curve that are located outside the reference threshold curves and wherein the deviation criteria is the maximum percentage of data points allowed to be outside of the reference threshold curves.

17. The method according to claim 15 further including calculating the sum of squares for threshold reference binding curve or sample binding curve where the reference curve has first been subtracted and using the ratio of the sum of squares as an evaluation criteria.

18. The biosensor system arranged to perform the method according to claim 15.

19. The computer program arranged to, when run on a computer, control the operation of a biosensor system to perform the method according to claim 17.

* * * * *

UNITED STATES PATENT AND TRADEMARK OFFICE
CERTIFICATE OF CORRECTION

PATENT NO. : 10,458,984 B2
APPLICATION NO. : 15/113352
DATED : October 29, 2019
INVENTOR(S) : Robert Karlsson Page 1 of 1

It is certified that error appears in the above-identified patent and that said Letters Patent is hereby corrected as shown below:

In the Claims

Claim 15, Column 14, Line 19:
Delete "reference".
Claim 16, Column 14, Line 28:
Replace "the" with "a".
Claim 17, Column 14, Line 34:
Replace "the" with "a".
Claim 17, Column 14, Line 36:
Replace "the" with "a", which currently reads "the ratio", so that the text reads "a ratio.".
Claim 19, Column 14, Line 40:
Replace "The" with "A".
Claim 19, Column 14, Line 41:
Replace "the" with "an".

Signed and Sealed this
Tenth Day of December, 2019

Andrei Iancu
*Director of the United States Patent and Trademark Office*